United States Patent
Xie et al.

(10) Patent No.: US 11,468,253 B2
(45) Date of Patent: Oct. 11, 2022

(54) INFORMATION PROCESSING APPARATUS AND METHOD FOR TISSUE PROCESSOR, AND INFORMATION PROCESSING SYSTEM

(71) Applicant: LEICA BIOSYSTEMS NUSSLOCH GMBH, Nussloch (DE)

(72) Inventors: Lingjun Xie, Shanghai (CN); Bao Zhang, Shanghai (CN)

(73) Assignee: LEICA BIOSYSTEMS NUSSLOCH GMBH, Nussloch (DE)

( * ) Notice: Subject to any disclaimer, the term of this patent is extended or adjusted under 35 U.S.C. 154(b) by 0 days.

(21) Appl. No.: 17/279,930

(22) PCT Filed: Nov. 5, 2019

(86) PCT No.: PCT/EP2019/080284
§ 371 (c)(1),
(2) Date: Mar. 25, 2021

(87) PCT Pub. No.: WO2020/094667
PCT Pub. Date: May 14, 2020

(65) Prior Publication Data
US 2021/0390275 A1    Dec. 16, 2021

(30) Foreign Application Priority Data
Nov. 5, 2018 (CN) .......................... 201811308113.2

(51) Int. Cl.
*G06K 7/10* (2006.01)
*G06K 7/14* (2006.01)
*G16H 10/40* (2018.01)

(52) U.S. Cl.
CPC ....... *G06K 7/10722* (2013.01); *G06K 7/1413* (2013.01); *G16H 10/40* (2018.01)

(58) Field of Classification Search
CPC ... G06K 7/10722; G06K 7/1413; G16H 10/40
USPC ................................................... 235/462.41
See application file for complete search history.

(56) References Cited

U.S. PATENT DOCUMENTS

| | | |
|---|---|---|
| 2009/0214088 A1 | 8/2009 | Sorenson et al. |
| 2012/0162358 A1* | 6/2012 | Choi ................ H04M 1/72469 345/173 |
| 2012/0197660 A1* | 8/2012 | Prodanovich .......... G16H 10/40 235/494 |
| 2013/0256405 A1 | 10/2013 | Montout |
| 2016/0085913 A1 | 3/2016 | Evans et al. |

* cited by examiner

*Primary Examiner* — Toan C Ly
(74) *Attorney, Agent, or Firm* — Hodgson Russ LLP (57) ABSTRACT

The present invention discloses an information processing apparatus (401) for a tissue processor (402). The tissue processor includes one or more sample baskets (403), a plurality of cassettes are located in each sample basket. The information processing apparatus (401) includes: a scanner, configured to scan a barcode containing information to be inputted to acquire a scan result; a camera, configured to capture at least one image for the plurality of cassettes in each sample basket; and a processor, configured to parse the scan result to acquire the information to be inputted and to process the at least one image to acquire an identification of each cassette. Further, the present invention provides an information processing system and an information processing method for a tissue processor.

14 Claims, 5 Drawing Sheets

INFORMATION PROCESSING APPARATUS AND METHOD FOR TISSUE PROCESSOR, AND INFORMATION PROCESSING SYSTEM

FIELD

The present invention relates to tissue processors, and more particularly to an information processing apparatus for a tissue processor, an information processing method for a tissue processor and an information processing system.

BACKGROUND

A tissue processor is an apparatus configured to enable tissue samples to immerge into a series of reagents in a reactor to process the tissue samples, for example, fixation, dehydration, osmotic treatment and the like. During processing of the tissue processor, it is important for a user to track information, such as sample information, operating record or the like. The information may include a user identification, a reagent identification, a basket identification, a cassette identification and so on. In related art, a barcode scanner is used to acquire the information for tracking.

In practice, the barcode scanner can acquire the user identification, the reagent identification, the basket identification, however, the barcode scanner is incapable to acquire the identifications of all cassettes quickly and timely since the identifications of some cassettes are handwriting marked or printed with no barcode.

SUMMARY

The present invention aims to solve the above problems in the related art to some extent.

Accordingly, a first objective of the present invention is to provide an information processing apparatus for a tissue processor, which can acquire information to be tracked in the tissue processor quickly and timely.

A second objective of the present invention is to provide an information processing system.

A third objective of the present invention is to provide an information processing method for a tissue processor.

In order to achieve the above objectives, embodiments of the present invention provide an information processing apparatus for a tissue processor. The tissue processor includes one or more sample baskets, a plurality of cassettes are located in each sample basket. The information processing apparatus includes: a scanner, configured to scan a barcode containing information to be inputted to acquire a scan result; a camera, configured to capture at least one image for the plurality of cassettes in each sample basket; and a processor, configured to parse the scan result to acquire the information to be inputted and to process the at least one image to acquire an identification of each cassette.

With the information processing apparatus for the tissue processor according to embodiments of the present invention, the barcode containing the information to be inputted is scanned by the scanner to acquire the scan result, the at least one image is captured by the camera for the plurality of cassettes in each sample basket, and the scan result is parsed by the processor to acquire the information to be inputted and the at least one image is processed to acquire the identification of each cassette. By combining scanning function and photographing function, the information processing apparatus can acquire information (such as user identification, reagent identification, basket identification, cassette identification) to be tracked in the tissue processor quickly and timely.

In an embodiment of the present invention, the information processing apparatus further includes a selector switch configured to switch the information processing apparatus between a scanner operation mode and a camera operation mode.

In an embodiment of the present invention, the information processing apparatus further includes a display screen configured to display a preview interface of the scanner or the camera and to display the scan result and the at least one image.

In an embodiment of the present invention, the information processing apparatus further includes: a cable, connected to the tissue processor, and configured to: supply power for the information processing apparatus; and transmit the scan result and the at least one image to the tissue processor or transmit the information to be inputted and the identification of each cassette to the tissue processor.

In an embodiment of the present invention, the information processing apparatus further includes: a power supply module, configured to supply power for the information processing apparatus; and a wireless transmission module, configured to transmit the scan result and the at least one image to the tissue processor or transmit the information to be inputted and the identification of each cassette to the tissue processor.

In an embodiment of the present invention, the processor is configured to process the at least one image to acquire the identification of each cassette by: identifying a barcode and text in the at least one image to acquire an identification of a cassette.

In an embodiment of the present invention, the processor is further configured to generate a sample report according to the information to be inputted and the identification of each cassette.

In an embodiment of the present invention, the sample report indicates the identification of each cassette through the at least one image and/or an identification list.

In order to achieve the above objectives, embodiments of the present invention provide an information processing system. The information processing system includes a tissue processor and an information processing apparatus for the tissue processor. The tissue processor includes one or more sample baskets, a plurality of cassettes are located in each sample basket. The information processing apparatus includes: a scanner, configured to scan a barcode containing information to be inputted to acquire a scan result; a camera, configured to capture at least one image for the plurality of cassettes in each sample basket; and a processor, configured to parse the scan result to acquire the information to be inputted and to process the at least one image to acquire an identification of each cassette.

The information processing system according to embodiments of the present invention includes the tissue processor and the information processing apparatus for the tissue processor. The tissue processor includes one or more sample baskets, a plurality of cassettes are located in each sample basket. The information processing apparatus scans the barcode containing the information to be inputted by the scanner to acquire the scan result, captures the at least one image by the camera for the plurality of cassettes in each sample basket, and parses the scan result by the processor to acquire the information to be inputted and processes the at least one image to acquire the identification of each cassette. By combining scanning function and photographing function, the information processing system can acquire information (such as user identification, reagent identification, basket identification, cassette identification) to be tracked in the tissue processor quickly and timely.

In an embodiment of the present invention, the information processing apparatus further includes a selector switch configured to switch the information processing apparatus between a scanner operation mode and a camera operation mode.

In an embodiment of the present invention, the information processing apparatus further includes a display screen configured to display a preview interface of the scanner or the camera and to display the scan result and the at least one image.

In an embodiment of the present invention, the information processing apparatus further includes: a cable, connected to the tissue processor, and configured to: supply power for the information processing apparatus; and transmit the scan result and the at least one image to the tissue processor or transmit the information to be inputted and the identification of each cassette to the tissue processor. The tissue processor is configured to: receive the scan result and the at least one image or receive the information to be inputted and the identification of each cassette; and parse the scan result to acquire the information to be inputted and to process the at least one image to acquire an identification of each cassette in response to receiving the scan result and the at least one image.

In an embodiment of the present invention, the information processing apparatus further includes: a power supply module, configured to supply power for the information processing apparatus; and a wireless transmission module, configured to transmit the scan result and the at least one image to the tissue processor or transmit the information to be inputted and the identification of each cassette to the tissue processor. The tissue processor is configured to: receive the scan result and the at least one image or receive the information to be inputted and the identification of each cassette; and parse the scan result to acquire the information to be inputted and to process the at least one image to acquire an identification of each cassette in response to receiving the scan result and the at least one image.

In an embodiment of the present invention, the processor is configured to process the at least one image to acquire the identification of each cassette by: identifying a barcode and text in the at least one image to acquire an identification of a cassette.

In an embodiment of the present invention, the processor is further configured to generate a sample report according to the information to be inputted and the identification of each cassette.

In an embodiment of the present invention, the sample report indicates the identification of each cassette through the at least one image and/or an identification list.

In order to achieve the above objectives, embodiments of the present invention further provide an information processing method for a tissue processor. The tissue processor includes one or more sample baskets, a plurality of cassettes are located in each sample basket. The information processing method includes: scanning a barcode containing information to be inputted to acquire a scan result; capturing at least one image for the plurality of cassettes in each sample basket; parsing the scan result to acquire the information to be inputted; and processing the at least one image to acquire an identification of each cassette.

With the information processing method for the tissue processor according to embodiments of the present invention, the barcode containing the information to be inputted is scanned to acquire the scan result, the at least one image is captured for the plurality of cassettes in each sample basket, and the scan result is parsed to acquire the information to be inputted and the at least one image is processed to acquire the identification of each cassette. By combining scanning function and photographing function, the information processing apparatus can acquire information (such as user identification, reagent identification, basket identification, cassette identification) to be tracked in the tissue processor quickly and timely.

In an embodiment of the present invention, processing the at least one image to acquire an identification of each cassette includes: identifying a barcode and text in the at least one image to acquire an identification of a cassette.

In an embodiment of the present invention, the method further includes: generating a sample report according to the information to be inputted and the identification of each cassette.

In an embodiment of the present invention, the sample report indicates the identification of each cassette through the at least one image and/or an identification list.

EMBODIMENTS OF THE PRESENT INVENTION

Reference will be made in detail to embodiments of the present invention. The embodiments described herein with reference to drawings are explanatory, illustrative, and used to generally understand the present invention. The embodiments shall not be construed to limit the present invention. The same or similar elements and the elements having same or similar functions are denoted by like reference numerals throughout the descriptions.

In order to implement a processing of a tissue processor, it is required to track information such as sample information and operating record during the entire processing. In the related art, the information to be tracked is typically acquired by a scanner. However, for the large amount of cassettes used in the tissue processor, it is hard to acquire information of the cassettes by the scanner quickly and timely.

Accordingly, the present invention provides an information processing method for a tissue processor, an information processing system and an information processing apparatus for a tissue processor. By combining scanning function and photographing function, the information to be tracked can be acquired timely and quickly.

Figure 1:
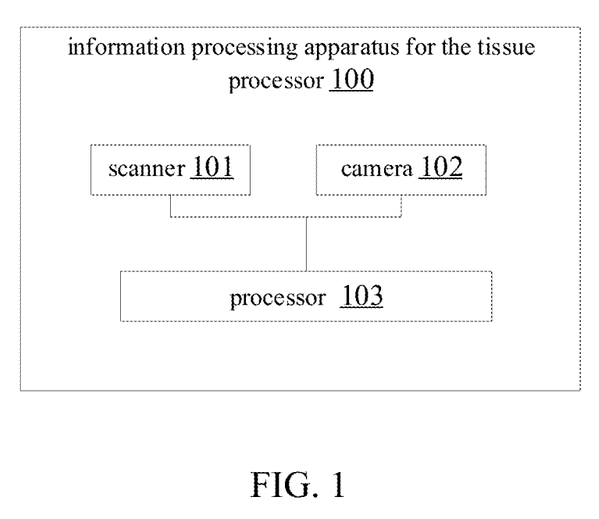
FIG. 1 is a block diagram of an information processing apparatus for a tissue processor according to an embodiment of the present invention.

FIG. 1 is a block diagram of an information processing apparatus for a tissue processor according to an embodiment of the present invention. As illustrated in FIG. 1, the information processing apparatus includes a scanner 101, a camera 102 and a processor 103.

Typically, the tissue processor includes one or more sample baskets, and a plurality of cassettes being located in each sample basket.

The scanner 101 is configured to scan a barcode containing information to be inputted to acquire a scan result. The barcode may be one dimensional barcode or two dimensional barcode. The information to be inputted may include a user identification, a sample basket identification, a reagent identification or the like.

The camera 102 is configured to capture at least one image for the plurality of cassettes in each sample basket.

The processor 103 is configured to parse the scan result to acquire the information to be inputted and to process the at least one image to acquire an identification of each cassette. In detail, when the processor 103 processes the at least one image, the processor 103 can be configured to identify barcode or text in the at least one image to acquire the identification of each cassette.

With the information processing apparatus for the tissue processor according to embodiments of the present invention, the barcode containing the information to be inputted is scanned by the scanner to acquire the scan result, the at least one image is captured by the camera for the plurality of cassettes in each sample basket, and the scan result is parsed by the processor to acquire the information to be inputted and the at least one image is processed to acquire the identification of each cassette. By combining scanning function and photographing function, the information processing apparatus can acquire information (such as user identification, reagent identification, basket identification, cassette identification) to be tracked in the tissue processor quickly and timely.

In embodiments of the present invention, the information processing apparatus integrates the scanning function and the photographing function. The scanning function can be used to scan the barcode with corresponding information to acquire the user identification, the sample basket identification, the reagent identification or the like. For example, a user may uses the information processing apparatus to scan an employee's card (the employee's card is printed with the barcode indicating an identity of the user) to acquire the user identification. Similarly, each sample basket is typically marked with the barcode indicating its identification, and the sample basket identification can be acquired by scanning the barcode. An external packing of the reagent is typically marked with the barcode indicating the identification of the reagent, such that the reagent identification can be acquired by scanning the barcode. However, since each sample basket may receive a plurality of cassettes, it is hard to acquire the cassette identifications of all the cassettes by scanning the barcode of each cassette quickly and timely. In addition, the identifications of some cassettes are not printed with the barcode or even the identifications of some cassettes are handwriting marked, such that it is impossible to acquire the identifications of those cassettes by scanning the barcode. In this case, the camera can capture one or more images for the plurality of cassettes in each sample basket. The identification of each cassette can be acquired by processing the one or more images.

Figure 2:
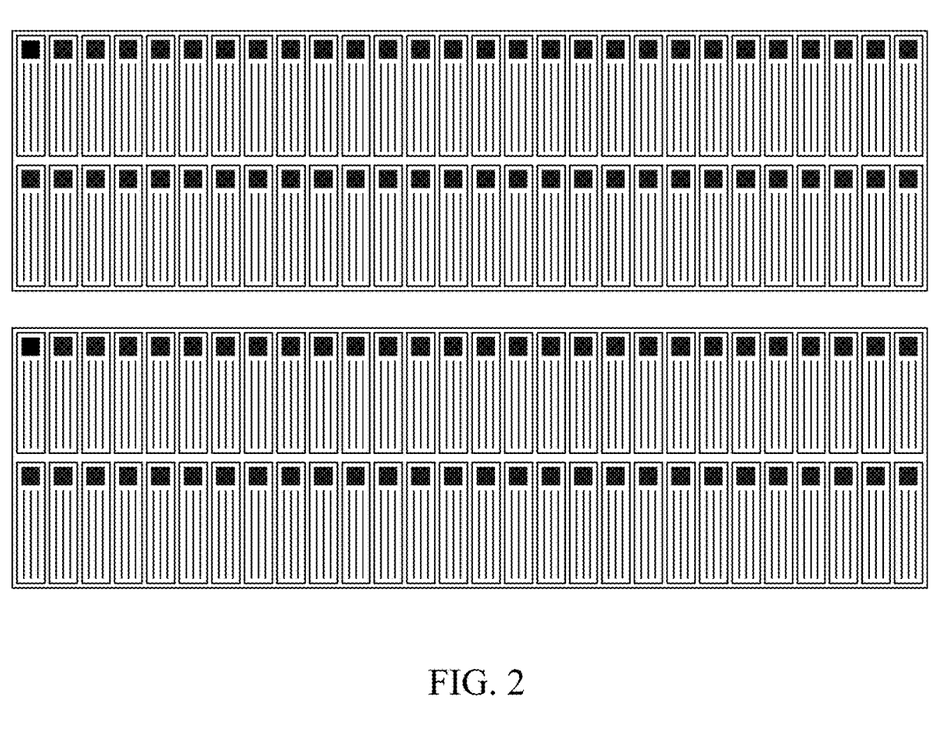
FIG. 2 is a schematic diagram illustrating an image of cassettes according to another embodiment of the present invention.

FIG. 2 is a schematic diagram illustrating an image of cassettes in one sample basket. As illustrated in FIG. 2, the image includes the identification of each cassette, barcode or the like. In FIG. 2, the shaded box on each cassette corresponds to a barcode (one-dimensional or two-dimensional), and the lines on each cassette correspond to lines of text. By parsing the image, for example, identifying the barcode and text in the image, the identification of each cassette can be acquired. Further, it should be noted that, due to the shooting angle, the photographed image may not include information of all the cassettes. In this case, the camera can be used to capture more images until all the necessary information of the plurality of cassettes can be acquired.

In an embodiment of the present invention, the information processing apparatus further includes a selector switch configured to switch the information processing apparatus between a scanner operation mode and a camera operation mode.

For different objects to be processed, it is required to make a choice between the scanning function and the photographing function to acquire corresponding information of the objects. The information processing apparatus is further provided with the selector switch. By means of the selector switch, it is convenient for the user to control the information processing apparatus to switch between the scanning function and the photographing function. For example, when the object to be processed is an employee's card, the selector switch is used to switch the information processing apparatus to the scanner operation mode, to utilize the scanner to scan the employee's card to acquire the user identification. When the object to be processed is a cassette, the selector switch is used to switch the information processing apparatus to the camera operation mode, to utilize the camera to capture one or more images for the plurality of cassettes in each sample basket, so as to acquire the identification of each cassette.

In an embodiment of the present invention, the information processing apparatus further includes a display screen configured to display a preview interface of the scanner or the camera and to display the scan result and the at least one image.

When using the scanner to scan the object to be processed or using the camera to capture an image of the object to be processed, if the scanner or the camera is not aligned with the object to be processed, the scan result or the image may be inaccurate. In order to avoid error in the scanning or capturing, the information processing apparatus further includes a display screen. The display screen may display the preview interface of the scanner or the camera, through which the user may determine whether the scanner or the camera is aligned with the object to be processed, such that the accurate scan result or image can be acquired. In addition, the display screen may further display the scan result or the image acquired by the scanner or the camera for review by the user.

In an embodiment of the present invention, the information processing apparatus further includes: a cable, connected to the tissue processor, and configured to: supply power for the information processing apparatus; and transmit the information to be inputted and the identification of each cassette to the tissue processor. The tissue processor receives the information to be inputted and the identification of each cassette for tracking during the processing of the tissue processor.

In some cases, the processor of the information processing apparatus cannot process the scan result or the image due to functionality and efficiency. To this end, the information processing apparatus may transmit the scan result and the at least one image to the tissue processor and the tissue processor parses the scan result to acquire the information to be inputted and processes the at least one image to acquire the identification of each cassette.

The cable not only can transmit the scan result and the at least one image to the tissue processor but also can supply power for the information processing apparatus.

However, in some embodiments, the information processing apparatus may further include: a power supply module, configured to supply power for the information processing apparatus; and a wireless transmission module, configured to transmit the scan result and the at least one image to the tissue processor or transmit the information to be inputted and the identification of each cassette to the tissue processor.

When the information processing apparatus is connected to the tissue processor through the cable, the position of the information processing apparatus can be limited at the proximity of the tissue processor, such that it is impossible to use the information processing apparatus to scan the barcode or capture the image for the object to be processed which is far way the tissue processor. In order to avoid the problem, the wireless transmission module and the power supply module can be used to implement functions of the cable.

In an embodiment of the present invention, the processor is further configured to generate a sample report according to the information to be inputted and the identification of each cassette.

The processor may further generate the sample report for review by the user. The sample report may include the user identification, the identification of each sample basket, the identification of each cassette or other information, such that the user may conveniently acquire sample information of each sample basket and each cassette during a sample processing performed by a certain user. The identification of each cassette can be shown in the sample report through the image of cassettes and/or an identification list. In other words, the sample report can provide the image of cassettes to show the identification of each cassette or can provide the identification list to show the identification of each cassette.

Figures 3, 4:
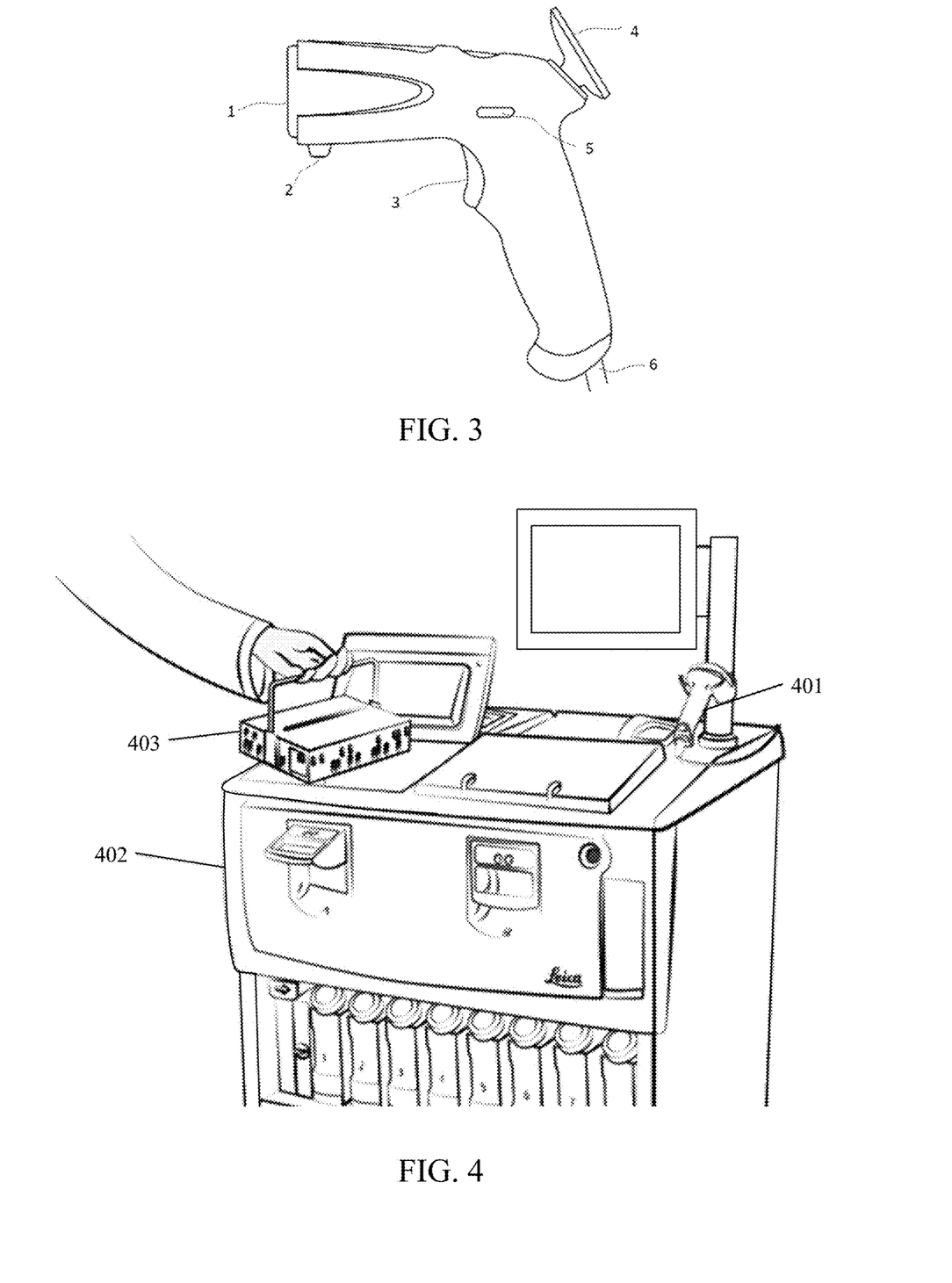
FIG. 3 is a lateral view of an information processing apparatus for a tissue processor according to an embodiment of the present invention.
FIG. 4 is a block diagram of an information processing system according to an embodiment of the present invention.

FIG. 3 is lateral view of an information processing apparatus for a tissue processor according to an embodiment of the present invention. As illustrated in FIG. 3, the information processing apparatus includes a scanner 1, a camera 2, a control switch 3, a display screen 4, a selector switch 5 and a cable 6. The processor is not shown in FIG. 3.

The information processing apparatus illustrated in FIG. 3 has a shape like a gun. The scanner 1 and the camera 2 are located in parallel at a location of the muzzle, which are both connected to the processor. The scanner 1 is configured to scan the barcode on the object to be processed, while the camera 2 is configured to capture the image of the object to be processed. The acquired scan result and image are transmitted to the processor for further processing. In FIG. 3, the camera 2 is beneath the scanner 1. However, it should be noted that, the camera 2 can be located above the scanner 1, or functions of the scanner 1 can be implemented by the camera 2. The control switch 3 is located at an upper part of a handle of the information processing apparatus. When the user holds the handle, a finger of the user may conveniently turn on or off the control switch 3, so as to turn on or off the information processing apparatus. The cable 6 extends from a bottom of the handle to be connected to the tissue processor. Through the cable 6, the information processing apparatus can acquire power and transmit the scan result and the image to the tissue processor. The display screen 4 is located at a side opposite to the muzzle-like part, such that the user may conveniently check information on the display screen 4. The selector switch 5 is located at the vicinity of the handle, such that the user may use the finger to control the selector switch 5, so as to enable the information processing apparatus to switch between the scanner operation mode and the camera operation mode.

FIG. 4 is a block diagram of an information processing system according to an embodiment of the present invention. As illustrated in FIG. 4, the information processing system may include an information processing apparatus 401 and a tissue processor 402. The tissue processor 402 includes one or more sample baskets 403. A plurality of cassettes can be placed in each sample basket. The information processing apparatus 401 includes a scanner, a camera and a processor. It should be noted that, although the information processing apparatus 401 is connected to the tissue processor 402 via a cable, the present invention is not limited to this. For example, the information processing apparatus 401 may be separated from the tissue processor 402 without the cable. In another embodiment, the information processing apparatus 401 and the tissue processor 402 can be integrated into a whole, for example, the information processing apparatus 401 may be integrated inside of the tissue processor 402.

The scanner is configured to scan a barcode containing information to be inputted to acquire a scan result. The barcode may be one dimensional barcode or two dimensional barcode. The information to be inputted may include a user identification, a sample basket identification, a reagent identification or the like.

The camera is configured to capture at least one image for the plurality of cassettes in each sample basket.

The processor is configured to parse the scan result to acquire the information to be inputted and to process the at least one image to acquire an identification of each cassette.

The information processing system according to embodiments of the present invention includes the tissue processor and the information processing apparatus for the tissue processor. The tissue processor includes one or more sample baskets, a plurality of cassettes are located in each sample basket. The information processing apparatus scans the barcode containing the information to be inputted by the scanner to acquire the scan result, captures the at least one image by the camera for the plurality of cassettes in each sample basket, and parses the scan result by the processor to acquire the information to be inputted and processes the at least one image to acquire the identification of each cassette. By combining scanning function and photographing function, the information processing system can acquire information (such as user identification, reagent identification, basket identification, cassette identification) to be tracked in the tissue processor quickly and timely.

In an embodiment of the present invention, the information processing apparatus 401 further includes a selector switch configured to switch the information processing apparatus between a scanner operation mode and a camera operation mode.

In an embodiment of the present invention, the information processing apparatus 401 further includes a display screen. Alternatively, the tissue processor 402 may include the display screen, as illustrated in FIG. 4. The display screen is configured to display a preview interface of the scanner or the camera and to display the scan result and the at least one image.

In an embodiment of the present invention, the information processing apparatus 401 further includes: a cable, connected to the tissue processor 402, and configured to: supply power for the information processing apparatus 401; and transmit the scan result and the at least one image to the tissue processor 402 or transmit the information to be inputted and the identification of each cassette to the tissue processor 402. The tissue processor 402 is configured to: receive the scan result and the at least one image or receive the information to be inputted and the identification of each cassette; and parse the scan result to acquire the information to be inputted and to process the at least one image to acquire an identification of each cassette in response to receiving the scan result and the at least one image.

In an embodiment of the present invention, the information processing apparatus 401 further includes: a power supply module, configured to supply power for the information processing apparatus 401; and a wireless transmission module, configured to transmit the scan result and the at least one image to the tissue processor 402 or transmit the information to be inputted and the identification of each cassette to the tissue processor 402. The tissue processor 402 is configured to: receive the scan result and the at least one image or receive the information to be inputted and the identification of each cassette; and parse the scan result to acquire the information to be inputted and to process the at least one image to acquire an identification of each cassette in response to receiving the scan result and the at least one image.

In an embodiment of the present invention, the processor is configured to process the at least one image to acquire the identification of each cassette by: identifying a barcode and text in the at least one image to acquire an identification of a cassette.

In an embodiment of the present invention, the processor is further configured to generate a sample report according to the information to be inputted and the identification of each cassette.

In an embodiment of the present invention, the sample report indicates the identification of each cassette through the at least one image and/or an identification list.

Figure 5:
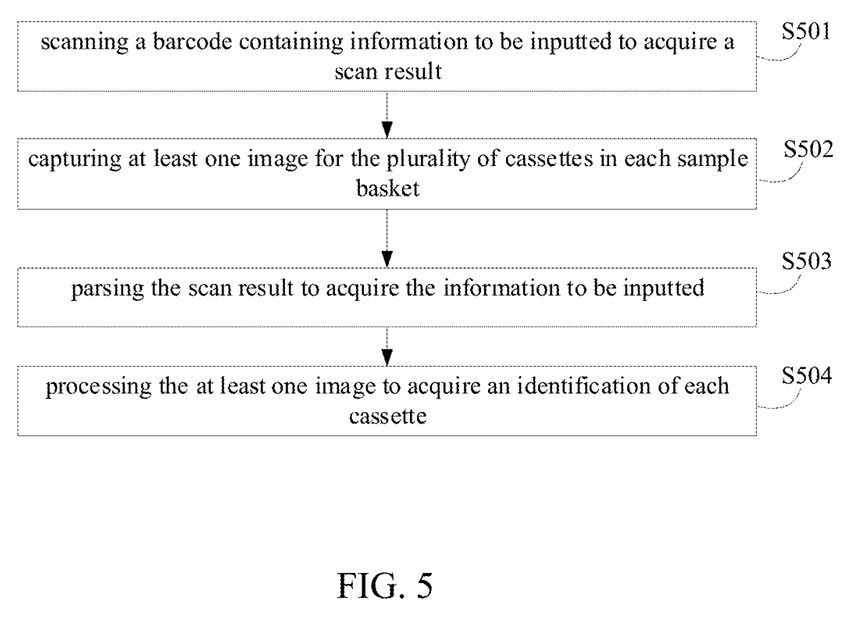
FIG. 5 is a flow chart of an information processing method for a tissue processor according to an embodiment of the present invention.

FIG. 5 is a flow chart of an information processing method for a tissue processor according to an embodiment of the present invention. As illustrated in FIG. 5, the method includes the followings.

At block 5501, a barcode containing information to be inputted is scanned to acquire a scan result.

At block 5502, at least one image is captured for the plurality of cassettes in each sample basket.

At block 5503, the scan result is parsed to acquire the information to be inputted.

At block 5504, the at least one image is processed to acquire an identification of each cassette.

With the information processing method for the tissue processor according to embodiments of the present invention, the barcode containing the information to be inputted is scanned to acquire the scan result, the at least one image is captured for the plurality of cassettes in each sample basket, and the scan result is parsed to acquire the information to be inputted and the at least one image is processed to acquire the identification of each cassette. By combining scanning function and photographing function, the information processing apparatus can acquire information (such as user identification, reagent identification, basket identification, cassette identification) to be tracked in the tissue processor quickly and timely.

In an embodiment of the present invention, processing the at least one image to acquire an identification of each cassette includes: identifying a barcode and text in the at least one image to acquire an identification of a cassette.

In an embodiment of the present invention, the method further includes: generating a sample report according to the information to be inputted and the identification of each cassette.

In an embodiment of the present invention, the sample report indicates the identification of each cassette through the at least one image and/or an identification list.

Figure 6:
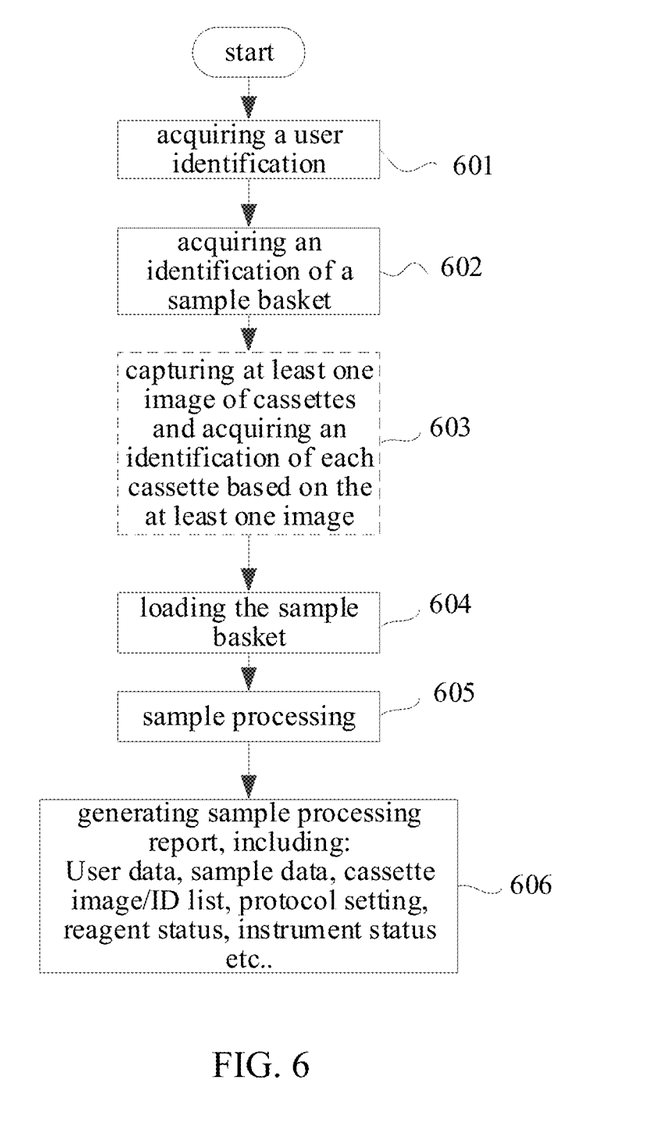
FIG. 6 is a flow chart of a processing of an information processing system according to an embodiment of the present invention.

FIG. 6 is a flow chart of a processing of an information processing system according to an embodiment of the present invention. As illustrated in FIG. 6, the processing includes the followings.

At block 5601, a user identification is acquired. The scanner in the information processing apparatus of the information processing system is used to scan the barcode containing the user identification to acquire the user identification.

At block 5602, an identification of a sample basket is acquired. The scanner is used to scan the barcode containing the identification of the sample basket and printed on the sample basket to acquire the identification of the sample basket.

At block 5603, at least one image of cassettes is captured and an identification of each cassette is acquired based on the at least one image. A camera in the information processing apparatus can be used to capture the cassettes in each sample basket to acquire the at least one image, and then the identification of each cassette is acquired on basis of the at least one image.

At block 5604, the sample basket is loaded. The sample basket is loaded into the tissue processor, such that the tissue processor can perform sample processing.

At block 5605, the sample processing is performed. The sample processing, for example, fixation, dehydration, osmotic treatment and the like is performed by the tissue processor.

At block 5606, a sample processing report is generated. The sample processing report can be generated according to the user identification, the identification of the sample basket, the identification of each cassette, a sample result, protocol setting, reagent status, and instrument status and so on.

During the above processing, the user identification, the identification of the sample basket, the identification of each cassette can be tracked.

In the specification, it is to be understood that terms such as "central," "longitudinal," "lateral," "length," "width," "thickness," "upper," "lower," "front," "rear," "left," "right," "vertical," "horizontal," "top," "bottom," "inner," "outer," "clockwise," and "counterclockwise" should be construed to refer to the orientation as then described or as shown in the drawings under discussion. These relative terms are for convenience of description and do not require that the present invention be constructed or operated in a particular orientation.

In addition, terms such as "first" and "second" are used herein for purposes of description and are not intended to indicate or imply relative importance or significance or to imply the number of indicated technical features. Thus, the feature defined with "first" and "second" may comprise one or more of this feature. In the description of the present invention, "a plurality of" means two or more than two, unless specified otherwise.

In the present invention, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

In the present invention, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present invention. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present invention. Furthermore, the particular features, structures, materials, or characteristics may be combined in any suitable manner in one or more embodiments or examples.

It will be understood that, the flow chart or any process or method described herein in other manners may represent a module, segment, or portion of code that comprises one or more executable instructions to implement the specified logic function(s) or that comprises one or more executable instructions of the steps of the progress. Although the flow chart shows a specific order of execution, it is understood that the order of execution may differ from that which is depicted. For example, the order of execution of two or more boxes may be scrambled relative to the order shown.

The logic and/or step described in other manners herein or shown in the flow chart, for example, a particular sequence table of executable instructions for realizing the logical function, may be specifically achieved in any computer readable medium to be used by the instruction execution system, device or equipment (such as the system based on computers, the system comprising processors or other systems capable of obtaining the instruction from the instruction execution system, device and equipment and executing the instruction), or to be used in combination with the instruction execution system, device and equipment. As to the specification, "the computer readable medium" may be any device adaptive for including, storing, communicating, propagating or transferring programs to be used by or in combination with the instruction execution system, device or equipment. More specific examples of the computer readable medium comprise but are not limited to: an electronic connection (an electronic device) with one or more wires, a portable computer enclosure (a magnetic device), a random access memory (RAM), a read only memory (ROM), an erasable programmable read-only memory (EPROM or a flash memory), an optical fiber device and a portable compact disk read-only memory (CDROM). In addition, the computer readable medium may even be a paper or other appropriate medium capable of printing programs thereon, this is because, for example, the paper or other appropriate medium may be optically scanned and then edited, decrypted or processed with other appropriate methods when necessary to obtain the programs in an electric manner, and then the programs may be stored in the computer memories.

It should be understood that each part of the present invention may be realized by the hardware, software, firmware or their combination. In the above embodiments, a plurality of steps or methods may be realized by the software or firmware stored in the memory and executed by the appropriate instruction execution system. For example, if it is realized by the hardware, likewise in another embodiment, the steps or methods may be realized by one or a combination of the following techniques known in the art: a discrete logic circuit having a logic gate circuit for realizing a logic function of a data signal, an application-specific integrated circuit having an appropriate combination logic gate circuit, a programmable gate array (PGA), a field programmable gate array (FPGA), etc.

Those skilled in the art shall understand that all or parts of the steps in the above exemplifying method of the present invention may be achieved by commanding the related hardware with programs. The programs may be stored in a computer readable storage medium, and the programs comprise one or a combination of the steps in the method embodiments of the present invention when run on a computer.

In addition, each function cell of the embodiments of the present invention may be integrated in a processing module, or these cells may be separate physical existence, or two or more cells are integrated in a processing module. The integrated module may be realized in a form of hardware or in a form of software function modules. When the integrated module is realized in a form of software function module and is sold or used as a standalone product, the integrated module may be stored in a computer readable storage medium.

The storage medium mentioned above may be read-only memories, magnetic disks, CD, etc.

Although explanatory embodiments have been shown and described, it would be appreciated by those skilled in the art that the above embodiments cannot be construed to limit the present invention, and changes, alternatives, and modifications can be made in the embodiments without departing fromspirit, principles and scope of the present invention.

What is claimed is:

1. An information processing apparatus for a tissue processor, the tissue processor comprising one or more sample baskets marked with a barcode indicating its identification, a plurality of cassettes being located in each sample basket, the information processing apparatus comprising:
    a scanner, configured to scan the barcode containing information to be inputted to acquire a scan result;
    a camera, configured to capture one image of the plurality of cassettes in each sample basket; and a processor, configured to parse the scan result to acquire a sample basket identification as the information to be inputted and to process the one image to acquire an identification of each cassette in the sample basket.

2. The apparatus according to claim 1, further comprising:
a selector switch, configured to switch the information processing apparatus between a scanner operation mode and a camera operation mode.

3. The apparatus according to claim 1, further comprising:
a display screen, configured to display a preview interface of the scanner or the camera and to display the scan result and the one image.

4. The apparatus according to claim 1, further comprising:
a cable, connected to the tissue processor, and configured to:
supply power for the information processing apparatus; and
transmit the scan result and the one image to the tissue processor or transmit the information to be inputted and the identification of each cassette to the tissue processor.

5. The apparatus according to claim 1, further comprising:
a power supply module, configured to supply power for the information processing apparatus; and
a wireless transmission module, configured to transmit the scan result and the one image to the tissue processor or transmit the information to be inputted and the identification of each cassette to the tissue processor.

6. The apparatus according to claim 1, wherein the processor is configured to process the one image to acquire the identification of each cassette by:
identifying a barcode and text in the one image to acquire an identification of a cassette.

7. The apparatus according to claim 1, wherein the processor is further configured to generate a sample report according to the information to be inputted and the identification of each cassette.

8. The apparatus according to claim 7, wherein the sample report indicates the identification of each cassette through the one image and/or an identification list.

9. An information processing system, comprising a tissue processor comprising one or more sample baskets, a plurality of cassettes being located in each sample basket, and an information processing apparatus according to claim 1.

10. The system according to claim 9, wherein the tissue processor is configured to:
receive the scan result and the one image or receive the information to be inputted and the identification of each cassette; and
parse the scan result to acquire the information to be inputted and to process the one image to acquire an identification of each cassette in response to receiving the scan result and the one image.

11. An information processing method for a tissue processor, the tissue processor comprising one or more sample baskets marked with a barcode indicating its identification, a plurality of cassettes being located in each sample basket, the information processing method comprising:
scanning the barcode containing information to be inputted to acquire a scan result;
capturing one image of the plurality of cassettes in each sample basket;
parsing the scan result to acquire a sample basket identification as the information to be inputted; and
processing the one image to acquire an identification of each cassette in the sample basket.

12. The method according to claim 11, wherein the step of processing the one image to acquire an identification of each cassette comprises:
identifying a barcode and text in the one image to acquire an identification of a cassette.

13. The method according to claim 11, further comprising:
generating a sample report according to the information to be inputted and the identification of each cassette.

14. The method according to claim 13, wherein the sample report indicates the identification of each cassette through the one image and/or an identification list.

* * * * *